US006015556A

United States Patent [19]
Bagshawe

[11] Patent Number: 6,015,556
[45] Date of Patent: *Jan. 18, 2000

[54] CYTOTOXIC DRUG THERAPY

[75] Inventor: Kenneth Dawson Bagshawe, London, United Kingdom

[73] Assignee: Enzacta R & D Limited, United Kingdom

[*] Notice: This patent is subject to a terminal disclaimer.

[21] Appl. No.: 08/885,281

[22] Filed: Jun. 30, 1997

Related U.S. Application Data

[63] Continuation of application No. 08/256,475, filed as application No. PCT/GB93/00039, Jan. 11, 1993, Pat. No. 5,658,568.

[30] Foreign Application Priority Data

Jan. 9, 1992 [GB] United Kingdom ............... 9200417

[51] Int. Cl.[7] .................. A61K 39/395; A61K 38/43; C07K 16/28; C07K 17/00
[52] U.S. Cl. .............................. 424/134.1; 514/2
[58] Field of Search .................. 514/2; 424/134.1, 424/94.1

[56] References Cited

U.S. PATENT DOCUMENTS 4,624,846  11/1986  Goldenberg.

FOREIGN PATENT DOCUMENTS

| 0 302 473 | 2/1989 | European Pat. Off. . |
|---|---|---|
| 0 308 208 | 3/1989 | European Pat. Off. . |
| 0 506 124 | 9/1992 | European Pat. Off. . |
| WO 88/06451 | 9/1988 | WIPO . |
| WO 88/07378 | 10/1988 | WIPO . |
| WO 89/10140 | 11/1989 | WIPO . |
| WO 90/10460 | 9/1990 | WIPO . |
| WO 91/09134 | 6/1991 | WIPO . |

OTHER PUBLICATIONS

Wu, G., et al., "Model for specific rescue of normal hepatocytes during methotrexate treatment of hepatic malignancy," *Proc. Natl. Acad. Sci. USA*, 80:3078–80 (1983).
Sauer, H., et al., "Biochemical Control of the Folinic Acid Rescue Effect After High–Dose Methotrexate (MTX) Therapy," *Chemistry and Biology of Pteridines*. pp. 683–688 (1979).
Riechmann, L., et al., "Reshaping human antibodies for therapy," *Nature*, 332(6162):323–27 (1988).
Wilkinson, I., et al., "Tolerance Induction in Mice by Conjugates of Monoclonal Immunoglobulins and Monomethoxypolyethylene Glycol," *The Journal of Immunology*, 139(2):326–31 (1987).
Jodrell, D.I., et al., "The renal effects of $N^{10}$–propargyl–5, 8–dideazafolic acid (CB3717) and a non–nephrotoxic analogue ICI D1694, in mice," *Br. J. Cancer*, 64:833–38 (1991).
Gilliland, L.K., et al., "Universal bispecific antibody for targeting tumor cells for destruction by cytotoxic T cells," *Proc. Natl. Acad. Sci. USA*, 85:7719–23 (1988).

Sharma, S.K., et al., "Inactivation and clearance of an anti–CEA carboxypeptidase G2 conjugate in blood after localisation in a xenograft model," *Br. J. Cancer*, 61:659–62 (1990).
Bosslet, K., et al., "Molecular and functional characterisation of a fusion protein suited for tumour specific prodrug activation," *Br. J. Cancer*, 65:234–38 (1992).
Morrison, S.L., et al., "Chimeric human antibody molecules: Mouse antigen–binding domains with human constant region domains," *Proc. Natl. Acad. Sci. USA*, 81:6851–55 (1984).
Huber, B.E., et al., "Retroviral–mediated gene therapy for the treatment of hepatocellular carcinoma: An innovative approach for cancer therapy," *Proc. Natl. Acad. Sci. USA*, 88:8039–43 (1991).
Bibby, C., et al., "Reduction of Tumor Blood Flow by Flavone Acetic Acid: A Possible Component of Therapy," *Journal of the National Cancer Institute*, 81(3):216–20 (1989).
Hennigan, T.W., et al., "Histamine, leukatriene C4 and interleukin–2 increase antibody uptake into a human carcinoma xenograft model," *Br. J. Cancer*, 64:872–74 (1991).
Smyth, M.J., et al., "Increased Antitumor Effect of Immunoconjugates and Tumor Necrosis Factor", Research Center for Cancer and Transplantation, University of Melbourne, Australia.
Harwood, P.J., et al., "Comparative Tumour Localization of Antibody Fragments and Intact IgG in Nude Mice Bearing a CEA–producing Human Colon Tumour Xenograft," *Eur J Cancer Clin Oncol*, 21(12):1515–22 (1985).
Melton, R.G., et al., "Covalent Linkage of Carboxypeptidase $G_2$ to Soluble Dextrans–I—Properties of Conjugates and Effects on Plasma Persistence In Mice," *Biochemical Pharmacology*, 36(1):105–12 (1987).
Melton, R.G., et al., "Covalent Linkage of Carboxypeptidase $G_2$ to Soluble Dextrans–II—In Vivo Distribution and Fate of Conjugates," *Biochemical Pharmacology*, 36(1):113–21 (1987).
Antoniw, P., et al., "Disposition of the prodrug–4–(bis(2–chloroethyl)amino) benzoyl–L–glutamic acid and its active parent drug in mice," *Br. J. Cancer*, 62:909–14 (1990).

(List continued on next page.)

*Primary Examiner*—Paula K. Hutzell
*Assistant Examiner*—Geetha P. Bansal
*Attorney, Agent, or Firm*—Nixon, Hargrave, Devans & Doyle LLP

[57] ABSTRACT

A compound comprises a target cell-specific portion, such as an antibody specific to tumor cell antigens, and an inactivating portion, such as an enzyme, capable of converting a substance which in its native state is able to inhibit the effect of a cytotoxic agent into a substance which has less effect against said cytotoxic agent. The prolonged action of a cytotoxic agent at tumor sites is therefore possible while protecting normal tissues from the effects of the cytotoxic agent.

2 Claims, 3 Drawing Sheets

OTHER PUBLICATIONS

Stephens, T.C. Dr., "Development of Anticancer Agents Acting Through Inhibition of Thymidylate Synthase", Bioscience 1, ICI Pharmaceuticals.

Chabner, B.A., et al., "Antitumor Activity of a Folate–cleaving Enzyme, Carboxypeptidase $G_1$," *Cancer Research*, 32:2114–19 (1972).

Bagshawe, K.D., "Antibody Directed Enzyme Prodrug Therapy," *Analytical Proceedings*, 27:5 (1990).

Melton, R.G., et al., "The potential of carboxypeptidase $G_2$: antibody conjugates as anti–tumour agents. II. In vivo localising and clearance properties in a choriocarcinoma model," *Br. J. Cancer*, 61:420–24 (1990).

Senter, P.D., et al., "Anti–tumour effects of antibody–alkaline phosphatase conjugates in combination with etiposide phosphate," *Proc. Natl. Acad. Sci. USA*, 85:4842–46 (1988).

Bertino, J.R., et al., "Inhibition of Growth of Leukemia Cells by Enzymic Folate Depletion," *Science*, 172:161–62.

Fernandes, D.J., et al., "5–Fluorouracil–methotrexate synergy: Enhancement of 5–fluorodeoxyuridylate binding to thymidylate synthase by dihydropteroylpolyglutamates," *Proc. Natl. Acad. Sci. USA*, 77(10):5663–67 (1980).

van Groeningen, C.J., et al., "Reversal of 5–Fluorouracil–Induced Myelosuppression by Prolonged Administration of High–Dose Uridine," *Journal of the National Cancer Institute*. 81(2):157–62 (1989).

Allegra, C.J., et al., "Trimetrexate for the Treatment of *Pneumocystis carinii* Pneumonia in Patients with the Acquired Immunodeficiency Syndrome," *The New England Journal of Medicine*, 317(16):978–85 (1987).

Priest, D.G., et al., "Pharmacokinetics of Leucovorin Metabolites on Human Plasma as a Function of Dose Administered Orally and Intravenously," *Journal of the National Cancer Institute*, 83(24):1806–12 (1991).

Searle, F., et al., "Carboxypeptidase G2 and Trimetrexate Cause Growth Delay of Human Colonic Cancer Cells In Vitro," *Biochemical Pharmacology*, 39(11):1787–91 (1990).

Kanellos, J., et al., "Studies of Methotrexate–Monoclonal Antibody Conjugates for Immunotherapy," *JNCI*, 75(2):319–29 (1985).

Morell, A.G., et al., "The Role of Sialic Acid in Determining the Survival of Glycoproteins in the Circulation," *The Journal of Biological Chemistry*, 246(5):1461–67 (1971).

Begent, R.H.J., "Targeted therapy: cell surface targets," *Science of Cancer Treatment*, pp. 161–184.

Begent, R.H.J., et al., "Second antibody for improvement of antibody imaging: liposome–entrapped and free preparations in animal and human studies," *Clin. exp. Immunol.*, 78:307–13 (1989).

Thornburg, R.W., et al., "Carbohydrate–mediated Clearance of Immune Complexes from the Circulation," *The Journal of Biological Chemistry*, 255(14):6820–25 (1980).

Haenseler, E., et al., "Activation of Methotrexate–α–Alanine by Carboxypeptidase A–Monoclonal Antibody Conjugate," *Biochemistry*, 31(3):891–97 (1992).

Barbet et al., "Specific Toxicity to activated T and B Lymphocytes of a Ricin A Immunotoxin Directed Against the Class I MHC Antigen, H–2 K," *Antibody, Immunoconjugates, Radiopharm*, 1(2):169–80 (1988).

Bagshawe, K.D., et al., *Br. J. Cancer*, 58:700–03 (1988).

ICI D1694

CYTOTOXIC DRUG THERAPY

This is a continuation, of application Ser. No. 08/256,475 filed on Jul. 8, 1994 U.S. Pat. No. 5,658,568, based on PCT/GB93/00039, filed Jan. 11, 1993.

This invention relates to potentially cytotoxic agents which may be targeted to selected cells, and is particularly concerned with the action of agents used in the treatment of cancer.

Most forms of cancer tend to disseminate in the body at an early stage and the ultimate aim of cancer therapy is to achieve elimination of cancers, preferably without incurring serious toxic effects on host systems. Combinations of cytotoxic agents have proved curative in a small range of relatively uncommon cancers, but single agents and combinations of them have failed to achieve major therapeutic benefits in most patients with the common cancers of lung, breast, colon, rectum, pancreas, prostate etc.

Cytotoxic agents can only be given by intermittent dose schedules because of their effects on normal tissues in which cell renewal is active such as haemopoietic tissues and epithelia of the alimentary tract. The rest period between treatments which is necessary to allow recovery of these normal tissues from the effects of the cytotoxic substances tends to be of much greater duration than the period of administration of the cytotoxic agents.

Substances involved in cell division are the commonest targets for cytotoxic agents and amongst these are substances involved in the synthesis of nucleotides, the basic components of DNA and RNA. The enzymes ribonucleotide reductase, dihydrofolate reductase and thymidine synthetase are typical targets. The enzyme dihydrofolate reductase acts on a dietary factor, folic acid, to produce the active co-enzyme 5,10-methenyltetrahydrofolate. The co-enzyme is required for one carbon transfer in various syntheses including that of pyrimidines required for DNA synthesis. The widely used drug methotrexate (2,4-diamino-$N^{10}$-methylpteroylglutamic acid) acts by binding strongly to dihydrofolate reductase preventing regeneration of active tetrahydrofolate and thus interrupting DNA synthesis and leading to death of cells entering S phase of the cell cycle in which DNA is duplicated. Methotrexate is generally available, for example from Cyanamid Inc.

The drug trimetrexate (NSC 352122; 2,4-diamino-5-methyl-6-[3,4,5-trimethoxyanilino methyl]quinazoline) also acts by binding to dihydrofolate reductase but whereas methotrexate enters cells via the folate receptors, trimetrexate enters by alternative mechanism(s). The synthesis of trimetrexate is disclosed by Baker (1967) in *Design of site-directed irreversible enzyme inhibitors*, Wiley, N.Y., and by Elsiager et al (1974) *Lectures in heterocyclic chemistry*, Vol. 2, pp 97/5–133 (Castle & Townsend, ed), Hetero Corp, Oren, Utah. Trimetrexate is generally available from US Biosciences, One Tower Bridge, 100 Front Street, Suite 400, West Conshohocken, Pa. 19428, USA.

Methotrexate resembles natural folates in having a terminal glutamic acid moiety which can be cleaved by carboxypeptidase G2, whereas trimetrexate is not susceptible to the action of this enzyme (Bagshawe (1985) *Clinical Radiol.* 36, 545–551). We have previously reported that the action of trimetrexate on colonic cancer cells in vitro can be enhanced by the addition to the culture medium of a folate degrading enzyme carboxypeptidase G2 (Searle et al (1990) *Biochemical Pharmacol.* 39, 1787–1791. We have also shown that this enzyme retains activity when conjugated to antibodies or antibody fragments (Searle et al (1988) *Bact. J. Cancer* 53, 377–384).

The biological effect of both methotrexate and trimetrexate can be reversed by administering an end product of the reaction they block, or by a more readily available analogue known as folinic acid [5-formyl tetrahydrofolic acid]. Folinic acid is widely available, for example as Lucovorin from Cyanamid Inc, but also from Wellcome Inc, and Farmitalia. If folinic acid is given in sufficient dosage concurrently with methotrexate or trimetrexate their actions are blocked. It has been found useful in the treatment of some cancers to use folinic acid in conjunction with methotrexate in carefully timed and dose controlled sequences. The methotrexate-folinic acid combination can improve the therapeutic ratio compared with methotrexate alone for certain cancers and is commonly known as 'rescue' therapy. It appears to depend on the ability of folinic acid to rescue normal clonogenic cells more readily than some cancer cells. One example is the successful use of methotrexate and folinic acid in the treatment of some trophoblastic tumours (Bagshawe et al (1989) *Brit. J. Ob. & Gynaecol.*). However this approach has proved useful in only a limited range of cancers and it seems likely that the time x concentration of folinic acid which is necessary to protect normal cells also protects some cancer cells from the action of the anti-folate.

Moreover the use of folinic acid in this way still necessitates intermittent administration of the methotrexate (MTX), whereas it would be advantageous to give the MTX more continuously over a prolonged period since it has been shown that the duration of action of anti-folates determines the degree of cytotoxicity achieved. Similar considerations apply to other cytotoxic drugs.

One aspect of the present invention provides a compound comprising a target cell-specific portion and an inactivating portion capable of converting a substance which, in its native state, is able to inhibit the effect of a cytotoxic agent into a substance which has less effect against said cytotoxic agent.

The inactivating portion may be directly or indirectly inactivating.

By "directly inactivating" we mean that the portion itself is able to inactivate the said substance, for example by binding to it or by converting it into an inactive form.

By "indirectly inactivating" we mean that delivery of the portion to the target cell results in inactivation of the cytotoxic agent. For example, the portion may be a nucleic acid, either DNA or RNA, that encodes a polypeptide that is able to inactivate the said substance, for example by binding to it or by converting it into an inactive form.

The said polypeptide may be expressed intracellularly, may be expressed on the cell surface, or may be secreted from the cell. By the term "polypeptide" we include proteins and glycoproteins.

Preferably, the inactivating portion is an enzymatically active portion.

Substances which "inhibit" the effect of a cytotoxic agent are those which diminish to a useful extent the ability of the cytotoxic agent to destroy target cells. Preferably, the said ability is reduced to substantially zero. Similarly, the inactivating portion will reduce such inhibition to a useful extent and will preferably reduce it to substantially zero.

The entity which is recognised by the target cell-specific portion may be any suitable entity which is expressed by tumour cells, virally-infected cells, pathogenic microorganisms, cells introduced as part of gene therapy or normal cells of the body which one wishes to destroy for a particular reason. The entity should preferably be present or accessible to the targeting portion in significantly greater concentrations in or on cells which are to be destroyed than in any normal tissues of the host that cannot be functionally replaced by other therapeutic means. Use of a target expressed by a cancer cell would not be precluded, for example, by its equal or greater expression on an endocrine tissue or organ. In a life-saving situation the organ could be sacrificed provided its function was either not essential to life, for example in the case of the testes, or could be supplied by hormone replacement therapy. Such considerations would apply, for instance, to the thyroid gland, parathyroids, adrenal cortex and ovaries.

The entity which is recognised will often be an antigen. Tumour-associated antigens, when they are expressed on the cell membrane or secreted into tumour extra-cellular fluid, lend themselves to the role of targets for antibodies.

The term "tumour" is to be understood as referring to all forms of neoplastic cell growth, including tumours of the lung, liver blood cells (leukaemias), skin, pancreas, colon, prostate, uterus or breast.

The antigen-specific portion may be an entire antibody (usually, for convenience and specificity, a monoclonal antibody), a part or parts thereof (for example an Fab fragment or $F(ab')_2$) or a synthetic antibody or part thereof. A conjugate comprising only part of an antibody may be advantageous by virtue of optimizing the rate of clearance from the blood and may be less likely to undergo non-specific binding due to the Fc part. Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies:

Techniques and Applications", J. G. R. Hurrell (CRC Press, 1982). All references mentioned in this specification are incorporated herein by reference. Bispecific antibodies may be prepared by cell fusion, by reassociation of monovalent fragments or by chemical cross-linking of whole antibodies, with one part of the resulting bispecific antibody being directed to the cell-specific antigen and the other to the enzyme. The bispecific antibody can be administered bound to the enzyme or it can be administered first, followed by the enzyme. It is preferred that the bispecific antibodies are administered first, and after localization to the tumour cells, the enzyme is administered to be captured by the tumour localized antibody. Methods for preparing bispecific antibodies are disclosed in Corvalan et al (1987) *Cancer Immunol. Immunother.* 24, 127–132 and 133–137 and 138–143, and Gilisland et al (1988) *Proc. Natl. Acad. Sci. USA* 85, 7719–7723.

The variable heavy ($V_H$) and vaiable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240. 1041); Fv molecules (Skerra et al (1988) *Science* 240. 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and $F(ab')_2$ fragments are "bivalent". By "bivalent" we mean that the said antibodies and $F(ab')_2$ fragments have two antigen combining sites. In contrast, Fab. Fv. ScFv and dAb fragments are monovalent, having only one antigen combining sites. Fragmentation of intact immunoglobulins to produce $F(ab')_2$ fragments is disclosed by Harwood et al (1985) *Eur. J. Cancer Clin. Oncol.* 21, 1515–1522.

IgG class antibodies are preferred.

Alternatively, the entity which is recognised may or may not be antigenic but can be recognised and selectively bound to in some other way. For example. it may be a characteristic cell surface receptor such as the receptor for melanocyte-stimulating hormone (MSH) which is expressed in high numbers in melanoma cells. The cell-specific portion may then be a compound or part thereof which specifically binds to the entity in a non-immune sense, for example as a substrate or analogue thereof for a cell-surface enzyme or as a messenger.

The virally directed enzyme-pro-drug therapy (VDEPT) approach has been disclosed for the selective killing of neoplastic cells using the transcriptional differences between normal and neoplastic cells to selectively drive expression of enzymes capable of converting a pro-drug into a cytotoxic drug (Huber et al (1991) *Proc. Natl. Acad. Sci. USA* 88, 8039–8043).

Thus, by analogy, transcriptional differences between normal and neoplastic cells may be used to selectively drive the expression of an enzyme capable of inactivating the inhibitor slubstances disclosed herein. It is preferred that the enzyme is secreted by the tumour cell, thus allowing free access to the inhibitor substance to be inactivated.

A difference in transcription between cells may be associated with tissue-specific promoters, or may be due to changes in activator or repressor molecules in the neoplastic state. Thus in one example, liver-associated albumin transcriptional regulatory sequences may be useful to drive the expression of inhibitor-inactivating proteins, including enzymes, in the treatment of patients with hepatocellular carcinoma. More transcriptional differences between normal and neoplastic cells are being discovered all the time, and it is believed that many of these differences may be exploited in the methods of the present invention.

Recombinant, replication-defective retroviruses which are suitable for delivering the genetic constructs (ie promoter plus gene encoding inhibitor-inactivating protein) to target cells have been disclosed (Huber et al (1991) *Proc. Natl. Acad. Sci. USA* 88, 8039–8043).

Thus, a virus or other nucleoprotein particle, or liposome may provide a target cell-specific portion suitable for delivering the indirectly inactivating portion to the said cell.

The inhibitor-inactivating protein may be an enzyme capable of metabolising the said inhibitor to an inactive form, or it may be a protein capable of binding the said inhibitor and hence inactivating it.

Considerable work has already been carried out on antibodies and fragments thereof to tumour-associated antigens and antibodies or antibody fragments directed at carcinoembryonic antigen (CEA) and antibodies or their fragments directed at human chorionic gonadotrophin (hCG) can be conjugated to carboxypeptidase G2 and the resulting conjugate retains both antigen binding and catalytic function. Following intravenous injection of these conjugates they localise selectively in tumours expressing CEA or hCG respectively. Other antibodies are known to localise in tumours expressing the corresponding antigen. Such tumours may be primary and metastatic colorectal cancer (CEA) and choriocarcinoma (hCG) in human patients or other forms of cancer. Although such antibody-enzyme conjugates may also localise in some normal tissues expressing the respective antigens. antigen expression is more diffuse in normal tissues. Such antibody-enzyme conjugates may be bound to cell membranes via their respective antigens or trapped by antigen secreted into the interstitial space between cells.

Examples of tumour-associated, immune cell-associated and infection reagent-related antigens are given in Table 1.

TABLE 1

| Antigen | Antibody | Existing Uses |
|---|---|---|
| 1. Tumour Associated Antigens | | |
| Carcino-embryonic Antigen | {C46 (Amersham) {85A12 (Unipath) | Imaging & Therapy of colon/rectum tumours. |
| Placental Alkaline Phosphatase | H17E2 (ICRF, Travers & Bodmer) | Imaging & Therapy of testicular and ovarian cancers. |
| Pan Carcinoma | NR-LU-10 (NeoRx Corporation) | Imaging & Therapy of various carcinomas incl. small cell lung cancer. |
| Polymorphic Epithelial Mucin (Human milk fat globule) | HMFG1 (Taylor-Papadimitriou, ICRF) | Imaging & Therapy of overian cancer, pleural effusions. |
| β-human Chorionic Gonadotropin choriocarcinoma | W14 | Targeting of enzyme(CPG2) to human xenograft in nude mice (Searle et al (1981) Br.J. Cancer 44, 137–144) |
| A carbohydrate on Human Carcinomas | L6 (IgG2a) 1 | Targeting of alkaline phosphatase (Senter et al (1988) Proc. Natl. Acad. Sci. USA 85, 4842–4846 |
| CD20 Antigen on B Lymphoma (normal and neoplastic) | 1F5 (IgG2a) 2 | Targeting of alkaline phosphatase (Senter et al (1988) Proc. Natl. Acad. Sci. 85, 4842–4846 |
| 2. Immune Cell Antigens | | |
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodme, Knowles ICRF, Licensed to Xoma Corp., USA) | Immunotoxin treatment of Acute Graft versus Host Disease, Rheumatoid Arthritis. |
| 3. Infectious Agent-Related Antigens | | |
| Mumps virus-related | Anti-mumps polyclonal | Antibody conjugated to Diphtheria toxin for |

TABLE 1-continued

| Antigen | Antibody | Existing Uses |
|---|---|---|
| | antibody | treatment of mumps. |
| Hepatitis B Surface Antigen | Anti HBs Ag | Immunotoxin against Hepatoma. |

1 Hellstrom et al (1986) Cancer Res. 46, 3917–3923
2 Clarke et al (1985) Proc. Natl. Acad. Sci. 82, 1766–1770
Other antigens include alphafoetoprotein, Ca-125 and prostate specific antigen.

Before the administration of a conjugate with an antibody directed at a tumour associated antigen it may be advantageous to augment the expression of that antigen at tumour sites since this may increase the amount of conjugate retained at tumour sites. Several agents have been identified as able to increase antibody uptake including tumour necrosis factor (TNF) (Forsyth et al (1988) Cancer Res. 48, 3607–3612) and interferons (Borden (1988) J. Nat. Cancer Inst. 80, 148–149).

Thus it is preferred that the expression of the tumour cell antigen is enhanced using any one or more of the reagents prior to or during the administration of the compound of the invention.

Uptake of an antibody, antibody fragment or any uptake thereof may also be modified by vasoactive agents through alterations in tumour blood flow or altering capillary permeability. Such agents include histamine and interleukin-2 (Hennigan et al (1991) Brit. J. Cancer 64, 872–874), flavone acetic acid (Bibby et al (1989) J. Natl. Cancer Institute 81, 216–219) but other agents may be used to alter tumour blood flow or capillary permeability so as to favour increased retention of enzyme at tumour sites or inhibit penetration of tumour sites by the protecting metabolite.

Thus it is further preferred that tumour blood flow is altered using one or more of the reagents prior to or during the administration of the compounds of the invention.

The substance which in its native state is able to inhibit the effect of a cytotoxic agent may be any sufficiently non-toxic substance which may be converted into a substance which has less effect on said cytotoxic agent. A suitable compound is folinic acid. Folinic acid reverses the biological effect of the cytotoxic agent trimetrexate, for example, which acts on the enzyme dihydrofolate reductase. Folinic acid is deglutamated and rendered inactive against trimetrexate by the enzyme carboxypeptidase G2 and other deglutamating enzymes.

The same principle may be applied to other anti-cytotoxic agent substances. For example, thymidine blocks the effect of a cytotoxic agent, such as CB3717 and ICI D1694 (Jodrell et al 1991, BJC 64, 833–8; Jones et al (1986) J. Med. Chem. 29, 468–472), which acts on the enzyme thymidylate synthetase. Hence a thymidine degrading enzyme (such as dihydrothymine dehydrogenase. Shiotani & Weber 1981 J. Biol. Chem. 256, 219–224) or thymidine kinase (Shiotani et al (1989) Cancer Res. 49, 1090–1094) may be used as the inactivating portion of the compound of the invention to render the thymidine ineffective against the cytotoxic agent.

Similar considerations relate to other agents which interfere with the normal processes of nucleotide incorporation into DNA or RNA since these are potentially reversible by the normal metabolite which in turn can be degraded by an appropriate enzyme targeted to tumour sites.

For instance, it has been shown that the cytotoxic effects of the widely used cytotoxic 5-fluorouracil (available from Roche Products Inc) can be at least partly attenuated by uridine (Groeningen et al (1989) *J. Natl. Cancer Inst.* 81, 157–162). It follows that conjugation of an antitumour antibody with a uridine degrading enzyme can be used in conjunction with 5-fluorouracil and uridine. Such a combination would be particularly relevant in colorectal and breast carcinoma for which 5-fluorouracil is one of the most effective cytotoxic agents. Such a combination of agents may be further combined with folinic acid which augments the cytotoxicity of 5-fluorouracil or additionally with thymidine and a thymidine inactivating enzyme.

The inactivating portion of the compound will be chosen by reference to the anti-cytotoxic agent substance.

Enzymes other than carboxypeptidase G2 and its equivalents can be used. They should be specific for the targeted metabolite but may be of human or non-human origin.

It may not be necessary to use a conventional enzyme. Antibodies with catalytic capacity have been developed (Tramontano et al *Science* 234. 1566– 1570) and are known as 'abzymes'. These have the potential advantage of being able to be humanized to reduce their immunogenicity.

Enzymes derived from human lymphocytes and able to degrade thymidine have been disclosed. (Schiotani et al (1989) *Cancer Res.* 49, 1090–1094). A dihydrothymine dehydrogenase and thymidine kinase can be used in the system of the type herein disclosed for use in conjunction with inhibitors of thymidine synthetase.

Thymidine degrading and phosphorylating enzymes can be used as an additional element in anti-folate therapy as herein disclosed by blocking the thymidine salvage pathway. They can also be used in conjunction with uridine catalysing enzymes used with the cytotoxic drug 5-fluorouracil.

The bacterial enzymes carboxypeptidase G1 and G2 (CPG1 and CPG2) degrade folates including methotrexate by cleavage of the terminal glutamic acid. The actions of the two enzymes are thought to be the same. The following description of preferred aspects of the invention refers to CPG2 but is equally applicable to CPG1 and to any other enzymes acting on the same substrates. and to abzymes acting on the same substrates.

The isolation, purification and some of the properties of carboxypeptidase G2 from Pseudomonas sp. strain RS-16 have been disclosed by Sherwood et al (1984) *Eur. J. Biochem.* 148, 447–453. The cloning of the gene encoding the said carboxypeptidase G2, its nucleotide sequence and its expression in *E. coli* have been disclosed by Minton et al (1984) *Gene* 31, 31–38 and Minton et al (1983) *J. Bacteriol.* 156, 1222–1227. CP2G2 is available from the Division of Biotechnology, Centre for Applied Microbiological Research, Porton Down, Salisbury, UK. Carboxypeptidase G1 (CPG1) is disclosed by Chabner et al (1972) *Cancer Res.* 32, 2114–2119.

It is likely that the inactivating portion of the compound, when it is an enzymatically active portion, will be enzymatically active in isolation from the cell-specific portion but it is necessary only for it to be enzymatically active when (a) it is in combination with the cell-specific portion and (b) the compound is attached to oriadjacent target cells.

The two portions of the compound of the invention may be linked together by any of the conventional ways of cross-linking polypeptides, such as those generally described in O'Sullivan et al (1979) *Anal. Biochem.* 100, 100–108. For example, the antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

It may not be necessary for the whole enzyme to be present in the compound of the invention but, of course, the catalytic portion must be present.

Alternatively, the compound may be produced as a fusion compound by recombinant DNA techniques whereby a length of DNA comprises respective regions encoding the two portions of the compound of the invention either adjacent one another or separated by a region encoding a linker peptide which does not destroy the desired properties of the compound. Conceivably, the two portions of the compound may overlap wholly or partly. The antibody component of the fusion must be represented by at least one binding site. Examples of the construction of antibody (or antibody fragment)-enzyme fusions are disclosed by Neuberger et al (1984) *Nature* 312. 604.

The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued Apr. 3, 1984 to Rutter et al, 4,530,901 issued Jul. 23, 1985 to Weissman, 4,582,800 issued Apr. 15, 1986 to Crowl, 4,677,063 issued Jun. 30, 1987 to Mark et al, 4,678,751 issued Jul. 7, 1987 to Goeddel. 4,704,362 issued Nov. 3, 1987 to Itakura et al, 4,710,463 issued Dec. 1, 1987 to Murray, 4,757,006 issued Jul. 12, 1988 to Toole, Jr. et al, 4,766,075 issued Aug. 23, 1988 to Goeddel et al and 4,810,648 issued Mar. 7, 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a procaryotic replicon, such as the ColE1 ori, for propagation in a procaryote, even if the vector is to be used for expression in other, non-procaryotic, cell types. The vectors can also include an appropriate promoter such as a procaryotic promoter capable of directing the expression (transcription and translation) of the genes in a bacterial host cell. such as *E. coli*. transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his3, trp1, leu2 and ura3. Plasmids pRS413–416 are Yeast Centromere plasmids (YCps).

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended. DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239. 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Exemplary genera of yeast contemplated to be useful in the practice of the present invention are Pichia, Saccharomyces, Kluyveromyces, Candida, Torulopsis, Hansenula, Schizosaccharomyces, Citeromyces, Pachysolen, Debaromyces, Metschunikowia, Rhodosporidium, Leucosporidium, Botryoascus, Sporidiobolus, Endomycopsis, and the like. Preferred genera are those selected from the group consisting of Pichia, Saccharomyces, Kluyveromyces, Yarrowia and Hansenula. Examples of Saccharomyces are *Saccharomyces cerevisiae, Saccharomyces italicus* and *Saccharomyces rouxii*. Examples of Kluyveromyces are *Kluyveromyces fragilis* and *Kluyveromyces lactis*. Examples of Hansenula are *Hansenula polymorpha, Hansenula anomala* and *Hansenula capsulata*. *Yarrowia lipolytica* is an example of a suitable Yarrowia species.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, and hybrid promoters involving hybrids of parts of 5' regulatory regions with parts of 5' regulatory regions of other promoters or with upstream activation sites (eg the promoter of EP-A-258 067).

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, ie may correspond to the promoter. Alternatively. they may be different in which case the termination signal of the *S. cerevisiae* AHD1 gene is preferred.

According to a further aspect of the present invention, there is provided a method of destroying target cells in a host, the method comprising administering to the host (i) a compound according to the present invention, (ii) a cytotoxic agent and (iii) a substance which in its native state is capable of inhibiting the effect of said cytotoxic agent and which can be converted by said inactivating portion into a substance which has less effect on the cytotoxic agent.

Preferably, the compound of the invention is administered and, once there is an optimum balance between the tumour to normal cell ratio of the compound and the absolute level of compound associated with the tumour, the cytotoxic agent together with the substance capable of blocking the effect of the cytotoxic agent are administered. However, an alternative method of administration would be possible. The amount of the compound of the invention circulating in the blood may be determined by measuring the activity of the enzymatic portion.

Preferably, the present invention provides a method of treating a mammal harbouring a tumour. Suitably, the mammal is first prepared for tumour therapy by administering a compound according to the present invention and allowing the ratio of compound bound to target cells to compound not bound to target cells to reach a desired value. The method then further comprises administering to the mammal a cytotoxic agent and a substance which in its native state is capable of inhibiting the effect of said cytotoxic agent from which a substance which has less effect on the cytotoxic agent can be generated by the inactivating portion of the said compound.

The compounds of the invention are administered in any suitable way, usually parenterally, for example intravenously, intraperitoneally or intra-vesically, in standard sterile, non-pyrogenic formulations of diluents and carriers, for example isotonic saline (when administered intravenously). The present invention therefore provides a means to allow continuous action of a cytotoxic agent at tumour sites whilst protecting normal tissues from the effects of the cytotoxic agent expressed by the target cancer. The substance which in its native state is capable of inhibiting the effect of the cytotoxic agent is given at a dose level sufficient to protect the normal tissues. However, the substance reaching tumour sites is inactivated before it can enter the cells and protect them from the cytotoxic agent. In this way normal tissues are protected from the effects of the cytotoxic agent whereas the protective molecule is rapidly degraded at tumour sites.

The cytotoxic agent and inhibitor are administered by any of the routes described for the compounds of the invention, and could also be administered orally.

It has also been shown that antibody-enzyme conjugates reach their peak concentration in tumours generally within 24 hours and that enzyme activity persists at tumour sites for up to 7–8 days. Antibody-enzyme conjugates also persist in blood and non-tumour tissues for several days. Enzyme in non-tumour tissues will degrade the inhibitor substance and thus tend to diminish its protective effect or increase the requirement for it. Clearance of enzyme from the blood can be accelerated or the enzyme can be inactivated without significantly altering enzyme levels in tumour sites by several techniques. These techniques may be employed usefully and additionally to the other components.

Although the antibodies or antibody fragments used in the antibody-enzyme conjugate can be 'humanised' to reduce their immunogenicity (as disclosed by Morrison et al (1984) *Proc. Natl. Acad. Sci. USA* 81, 6851–6855 and Riechmann et al (1988) *Nature* 332, 323–327), the bacterial enzymes CPG1 and CPG2 have no human analogue and for repeated use in man it may be desirable to modify them so as to reduce their immunogenicity or to employ means to induce immunosuppression or immune tolerance.

Techniques for reducing the immunogenicity of foreign proteins, applicable to antibody-enzyme conjugates, include that of conjugation to forms of polyethylene glycol (Wilkinson et al (1987) *J. Immunol.* 139, 326–331).

Alternatively, or additionally, the problem of immunogenicity may be overcome by administering immunosuppressors or immune tolerance inducing agents. Cyclosporin and FK506 are Widely used drugs to achieve immunosuppression in tissue transplantation. Cyclosporin has been shown to delay host antibody respone to foreign protein (Lederman et al (1988) *Br. J. Cancer* 58. 562–566 and 654–657). Tolerance to foreign proteins when the host encounters the foreign problem for the first time after receiving an antibody directed at the CD4 epitope on lymphocytes has been disclosed (Waldman et al (1988) pp 16–30 in *Progress in Allergy* (Shizata & Woksman, Eds, N.Y.). Further means to achieve this have been described elsewhere and may change as improvements occur in control of host antibody responses to foreign antigens. Catalytic antibodies (abzymes) may be 'humanized' to reduce or remove their immunogenicity.

When an antibody directed at a tumour associated antigen or an antibody-enzyme conjugate is injected into an appropriate tumour bearing host. only a small fraction of the antibody or conjugate localises at the tumour site and most of it remains in blood and other normal tissues for several days. Thus, although tumour concentration of the enzyme will be higher than in normal tissues, the volume of normal tissues is much greater. Thus, to minimize the amount of enzyme residual in normal tissues and blood it may be desirable to use the methods of the present invention in conjunction with the methods disclosed in WO 89/10140; Bagshawe (1989) *Brit. J. Cancer* 60, 275–281; and Sharma et al (1990) *Brit. J. Cancer* 61, 659–662 for inactivating and clearing excess antibody-enzyme conjugate from the blood.

In attempting to achieve eradication of cancers it may not be possible. to avoid suppression of haemopoietic function although for a given effect on a tumour target (myelosuppression) it is expected to be much less with the system described herein. Similarly, for a given degree of myelosuppression a much greater tumour effect is expected. Growth factors acting on haemopoletic tissues may therefore be usefully employed in combination with the system described herein.

The system described herein may be used in conjunction with other forms of therapy. These include conventional cytotoxic agents, and use of multiple enzyme delivery to inactivate more than one metabolite.

Similarly, an enzyme delivered to tumour sites by an antibody may function both to activate a pro-drug and to inactivate a metabolite which protects normal tissues. Carboxypeptidase G2 as disclosed herein inactivates folinic acid at tumour sites to leave the tumour cells unprotected against trimetrexate. The same tumour located enzyme can activate a benzoic acid pro-drug to form a cytotoxic mustard (as disclosed by Bagshawe (1989) *Brit. J. Cancer* 60. 275–281).

Of course, one or more enzymes may be directed to the tumour sites either by the same or a different antibody, and such that one or more prodrugs are converted to an active drug, and that one or more protective agents are degraded at the tumour site. Thus, two or more enzymes may be joined to the same antibody.

Since antibody-enzyme conjugates generally reach their maximum concentration at tumour sites within 12–24 hours and since they may take several days to clear from plasma and other body fluids, it has also been shown that it is advantageous to accelerate the clearance of antibody-enzyme conjugate and to inactivate the specific enzyme present in the blood. Several means by which this may be achieved have been described (WO 89/10140).

The antibody used for cleavtng or inactivating the antibody-enzyme conjugate can be directed towards the antigen binding site on the antitumour antibody, or the active site of the enzyme, or any other site on the antibody-enzyme conjugate. Such antibodies may have additional galactose residues or other sugars added to accelerate clearance or may be desialylated. Galactosylation of the antibody results in its rapid clearance from the blood through take-up by galactose receptors on hepatocytes. Alternatively, or additionally, the antibody-enzyme conjugate is galactosylated, and given after the hepatic galactose receptors have been blocked by asialo-bovine submaxillary gland mucoprotein or antibody directed at hepatic galactose receptor or other molecule with high affinity for galactose receptor. The blocking substance is maintained in plasma for a period of up to 24 hours so that the antibody-enzyme complex localises at tumour sites but following cessation of galactose receptor blockade, the galactosylated antibody-enzyme is quickly cleared via the available galactose receptors.

The present invention will now be illustrated by way of the following Examples and Figures with specific references to cytotoxic therapy with trimetrexate and folinic acid rescue.

Figure 1A:
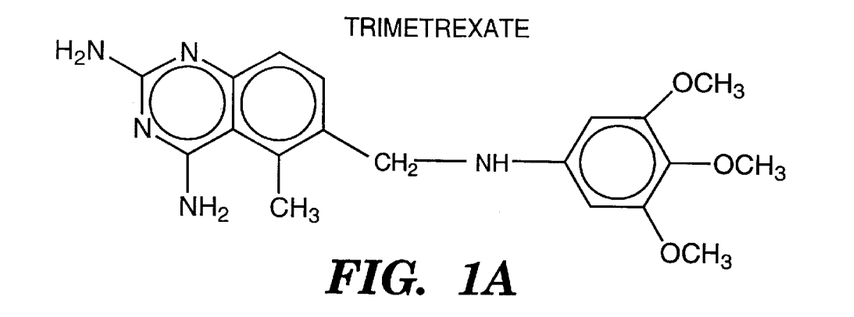
FIG. 1 shows the structures of trimetrexate, methotrexate, folinic acid. CB3717 and ICI D1694.
Figure 1B:
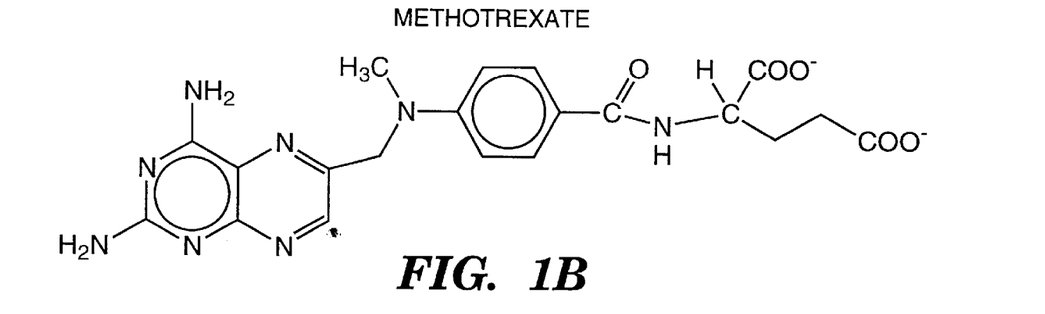
Figure 1C:
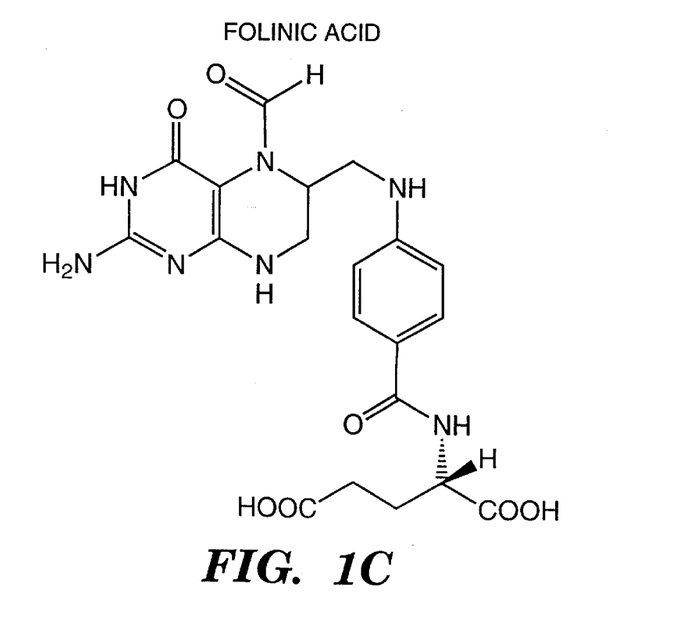
Figure 1D:
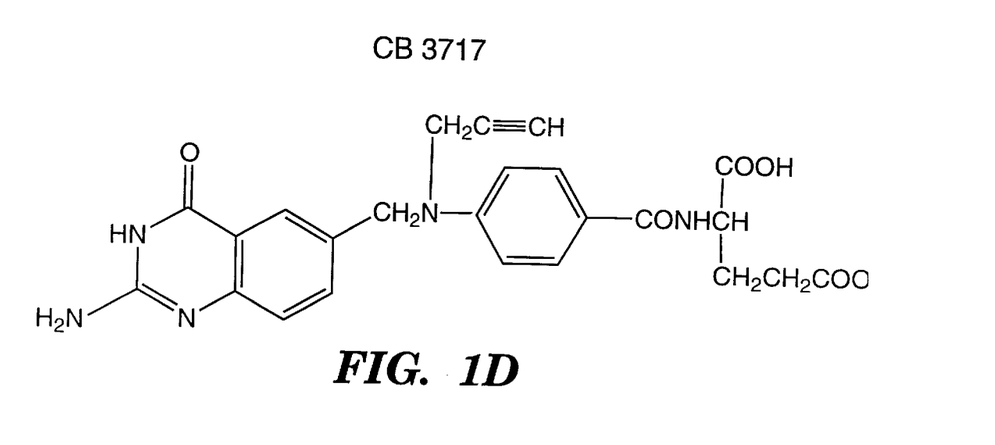
Figure 1E:
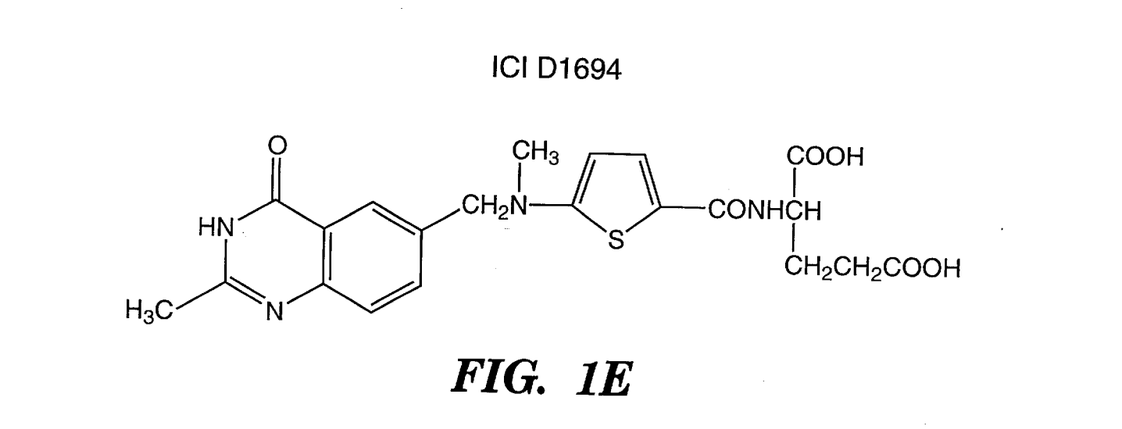
Figure 2:
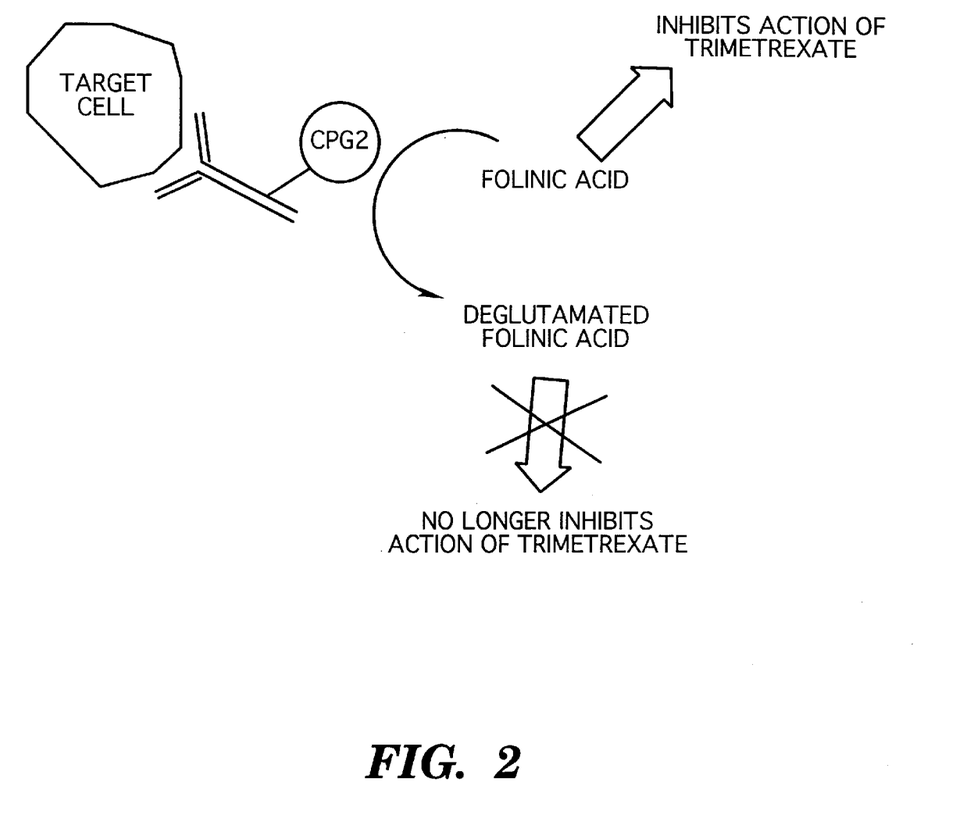
FIG. 2 is a diagrammatic representation of the invention wherein the target-cell specific portion is an antibody and is coupled to carboxypeptidase G2; folinic acid is the inhibitor of a cytotoxic agent; and trimetrexate is the said cytotoxic agent.

EXAMPLE 1
Cytotoxic Therapy with Trimetrexate and Folinic Acid Rescue

The present invention may provide a means to allow more continuous anti-folate action at tumour sites whilst protecting normal tissues from anti-folate effects. The first step is to initiate immunosuppressive or immune tolerance inducing agents and this will normally occur not less than 2 days before the compound of the present invention is administered. If the antibody-enzyme conjugate is non-immunogenic this step is omitted. An antibody-CPG2 conjugate, or antibody fragment conjugated chemically or by recombinant DNA technology to CPG2 or similar enzyme is given by intravenous or other appropriate route; the antibody is directed at a tumour antigen expressed by the target cancer. After several hours has been allowed for the conjugate to localise at tumour sites a second antibody is given. This may be directed at the active site on the enzyme in which case additional galactose residues are attached to the second antibody to ensure its rapid clearance via hepatocyte galactose receptors. Alternative mechanisms for rapid clearance of the conjugate from non-tumour sites have been described. When enzyme levels have fallen to very low or undetectable levels in plasma, trimetrexate is given by bolus or by continuous infusions with the aim of maintaining a constant plasma concentration. Concurrently with the trimetrexate, folinic acid is given by intravenous infusion at a dose level sufficient to protect the normal tissues from trimetrexate toxicity. Folinic acid reaching tumour sites where CPG2 is located is deglutamated as is folic acid and rendered inactive before it can enter cells and protect them from trimetrexate. In this way normal tissues may be protected by folinic acid from the action of trimetrexate whereas the protective molecule is rapidly degraded at tumour sites. Other antifolate drugs which, like trimetrexate are not degraded by CPG2, may be substituted for trimetrexate.

Since the trimetrexate blockade of dihydrofolate reductase may be, at least partially, bypassed by endogenous sources of thymidine, a thymidine-degrading enzyme might also be targeted to tumour sites by antibody or other ligand.

It is recognised that distribution of the antibody-enzyme conjugates in the tumour will not be uniform since there is heterogeneity in the expression of tumour-associated antigens on cell membranes. Secretion of an antigen into extracellular space results in more uniform distribution of target antigen and secreted antigen forms complexes with targeted antibody-enzyme, conjugate. Internalisation of the antibody-enzyme conjugate by tumour cells is not necessary and may be undesirable.

It is evident that the method according to the present invention differs from conventional cytotoxic chemotherapy with methotrexate and folinic acid rescue by the introduction of a means of degrading the normal metabolite (folic acid) and the rescue agent (folinic acid) but not the folic acid antagonist at tumour sites.

Loss of enzyme from tumour sites by dissociation of the antibody from target antigen and by biodegradation are likely to result after some days in reduced levels of enzyme at those sites. The rate of fall in enzyme activity will vary with tumour and enzyme type; carboxypeptidase activity has been detected in human colonic carcinoma xenografted tumours in nude mice 7 days after administration conjugated to an antibody directed at CEA. It should therefore be possible to continue trimetrexate therapy for about 5 days with an interruption about 24–48 hours, during which time further antibody-enzyme conjugate could be given and cleared from non-tumour sites with further cycles to follow provided there is effective immunological control or avoidance of host antibody response.

Thus although the proposal would not result in uninterrupted therapy the ratio of treatment period to treatment free period in conventional therapy of about 1:7 would be improved to about 2–3:1.

EXAMPLE 2
Cytotoxic Therapy with Thymidylate Synthetase Inhibitors and Thymidine Rescue.

The same principle may be applied to other anti-metabolite therapies. For instance, considerable effort has been directed in recent years to the development of agents that block the key enzyme thymidylate synthetase such as CB3717 and ICI D1694 (Jodrell et al 1991. *BJC* 64, 833–8). Such agents are likely to suffer the same limitations as conventional cytotoxic agents in that they also block thymidylate synthetase in normal cells. Their action is reversible by thymidine. Thymidine administration may therefore be used to protect normal tissues from thymidylate synthetase inhibitors whilst the protective effect of the thymidine and endogenous thymidine may be limited at tumour sites by a thymidine degrading enzyme, such as dihydrothymine dehydrogenase, or thymidine kinase which would inhibit entry of thymidine into the tumour cells. The thymidine inhibitor enzyme or agent is delivered by antibody or other appropriate vector.

Dihydrothymine dehydrogenase can be obtained from normal human lymphocytes (Shiotani & Weber 1989 *Cancer Res.* 49, 1090–1094) and therefore has the advantage that an antibody-enzyme conjugate of low immunogenicity may be produced by its conjugation to a human or 'humanised' antibody.

It is also envisaged that both an antifolate agent and an anti-thymidine agent could be used together with the appropriate inhibitors and inhibitor degrading enzymes resulting in an effective cytotoxic combination.

EXAMPLE 3
Combination Therapy with ADEPT

The ADEPT concept uses an antibody-enzyme conjugate to generate a cytotoxic drug from an inactive precursor at tumour sites. The present invention can be used in conduction with ADEPT thus resulting in a form of combination chemotherapy, both active drugs being confined largely to the tumour site but employing the same, or different enzymes to produce the active agent in one case and to destroy a protective agent in the other.

In the case of ADEPT treatment, nude mice bearing human choriocarcinoma (CC3) tumours received 29 units of CPG2 conjugated to anti-HCG (W14 $Fab_2$, as disclosed in WO 88/07378), and after 24 or 48 hours received pro-drug

EXAMPLE 4
Treatment of Patient with Hepatic Metastases and Abdominal Adenocarcinoma Starting on day minus-2 a patient with large hepatic metastases and recurrent abdominal adenocarcinoma of the colon received the immunosuppressive agent cyclosporin by continuous intravenous infusion. On day 0 he received a compound containing the F(ab')$_2$ portion of a monoclonal antibody known as A$_5$B$_7$ which binds carcinoembryonic antigen (CEA) chemically conjugated to carboxypeptidase G2 a bacterial enzyme. The amount of enzyme given was 20000 enzyme units (10,000 U/M$^2$) by intravenous infusion over 2 hours. 24 hours later (day 1) the enzyme was still available in his blood plasma at 1.0 unit/ml and he then received 80 mg (40 mg/m$^2$) of monoclonal antibody SB43 which had been galactosylated to accelerate its clearance. This was administered over 24 hours by continuous intravenous infusion and during the last hour of the infusion 10 mg of non-galactosylated SB43 was added to the infusate. Following completion of the SB43 infusion (day 2) when CPG2 activity was no longer detectable in plasma, trimetrexate was given in 5% dextrose by intravenous bolus. Infusion of folinic acid 100 mg commenced at this time by continuous 24 hour infusion. Trimetrexate was continued daily for 4 days (day 2, 3, 4, 5).

The cycle starting with the antibody enzyme conjugate restarted on days 7 and 14. Toxicity was confined to a temporary rise in serum creatine, a well-known complication of therapy with cyclosporin. The host antibody response to the tumour antibodies and bacterial enzymes was not detectable until after completion of the three cycles of treatment.

The peripheral blood white cell and platelet counts remained at normal or supranormal levels during and after this treatment. Subsequent patients receive escalating doses of trimetrexate or reduced doses of folinic acid.

The monoclonal antibody A$_5$B$_7$, raised in mice to carcinoembryonic antigen (CEA), is available from Cancer Research Campaign Technology, Cambridge House, 5–10 Cambridge Terrace, Regent's Park, London NW1 4JL, and was prepared by the method disclosed by Harwood et al (1986) *Brit. J. Cancer* 54, 75–82 and Example 5. The murine monoclonal antibody SB43 is available from Cancer Research Campaign Technology and was prepared by the method disclosed by Sharma et al (1990) *Brit. J. Cancer* 61, 659–662 and Example 8.

EXAMPLE 5
Preparation of a Monoclonal Antibody Reactive Against Carcinoembryonic Antigen Purified CEA was prepared from metastases of colonic tumour. Radio-iodination to a specific activity of 6 $\mu$Ci$\mu$g$^{-1}$ was carried out by the iodogen method. Dilution buffer was prepared as a 0.15M sodium phosphate buffer, pH 7.4, containing 0.1% bovine serum albumin. The studies at low ionic strength were carried out in 0.02M Tris-HCl buffer at pH 7.4.

Immunisation schedule: Monoclonal antibody A$_5$B$_7$ was raised against purified, heat-treated CEA using the following procedure. One milligram of purified CEA was heated at 85° C. for 35 min in 0.05 M phosphate buffer (pH 7) at a concentration of 1 mg ml$^{-1}$. After mixing with 1 ml of 10% aqueous potassium aluminium sulphate (alum), the pH was adjusted with constant stirring to 6.5–7 by dropwise addition of NaOH solution. After stirring at room temperature for 30 min the resulting precipitate was washed three times in saline. It was then mixed with 10$^{10}$ forinalised *Bordetella pertussis* (kindly supplied by Wellcome Research Laboratories). Three different immunisation schedules were used.

Spleen cells from the immunised mice were then fused with either SP2/0-Ag 14 or P3-NS/1-Ag 4-1 myeloma cells (Flow Laboratories, UK) and the hybridomas producing anti-CEA cloned by single cell transfer.

EXAMPLE 6
Preparation of F(ab')$_2$ Fragments of A$_5$B$_7$

The monoclonal anti-CEA (A$_5$B$_7$) used in this study has been described previously and chosen for its low cross-reactivity with NCA and its stability on immunopurification and radiolabelling. F(ab')$_2$ fragments were prepared by the method Lamoyi and Nisonoff (1983) *J. Immunol. Methods* 56, 235–243. After separation of the digest mixture on Sephacryl S-200, the fractions were analysed by SDS-PAGE using a 7.5% gel. The fraction containing the F(ab')$_2$ was concentrated and dialysed against 0.15M phosphate buffer, pH 7. Both intact A$_5$B$_7$ and the fragment were shown to be immunologically active and relatively homogeneous by electroblotting of the SDS gel onto nitrocellulose paper and overlaying with $^{125}$I-labelled CEA. Intact A$_5$B$_7$ and its F(ab')$_2$ fragment were radiolabelled by the chloramine T method to specific activities of 5.6 and 5.2 $\mu$Ci/$\mu$g respectively. Both labelled preparations were shown to retain immunological activity by solid-phase radioimmunoassay using CEA coupled to amino-cellulose (Rodgers et al (1983) *Eur. J. Cancer Clin. Oncol.* 19, 629–639). An excess of 60% activity was retained in each case.

EXAMPLE 7
Conjugation of A$_5$B$_7$-F(ab')$_2$ to CPG2

To a solution of CPG2 (2.15 mg) in phosphate buffer (2.5 ml, pH=7.6, containing 1 mM EDTA) was added 4-(p-maleimidophenyl) butyric acid N-hydroxysuccinimide ester (138 $\mu$g) in DMF (13.5 $\mu$l) corresponding to a 15 molar excess of ester over carboxypeptidase. The solution was left for 2 hours after which time excess ester was removed by gel filtration (PD10 column), eluted with 3.2 cm phosphate/EDTA buffer)—Solution 1.

F(ab')$_2$-A$_5$B$_7$ (2.6 mg) in phosphate/EDTA buffer (1.2 ml) was treated with S-acetyl thioglycol acid-N-hydroxysuccinimide ester (SATA) (90 $\mu$g) in DMF (10 $\mu$l) and the mixture left for 1 hour at room temperature. Excess SATA was removed by gel filtration (PD10 column, eluted with 3.2 cm phosphate buffer).

Thirty minutes before use, a solution of NH$_4$OH (3.47 g neutralised with Na$_3$PO$_4$H and NaOH solution and made up to 100 ml with H$_2$O containing 930 mg EDTA)(320 $\mu$l) was added—Solution 2.

The solutions 1 and 2 were then mixed and allowed to stand at 4° C. overnight. After concentration (ten-fold) (Minicon) the conjugate was isolated by gel filtration (S-12 column) on FPLC (Pharmacia). The conjugate was filtered through a Millipore 0.22 $\mu$m filter. The protein concentration was measured and the enzyme activity measured on spectrophotometric assay before use.

EXAMPLE 8
Production of a Monoclonal Antibody Reactive Against CPG2

A monoclonal antibody (SB43) raised against CPG2 is used for making bispecific antibody (see next-Example) and for clearance and inactivation of residual enzyme activity at non-tumour sites.

The monoclonal antibody was made in the following way. Balb/C mice (6–8 weeks old) were immunised with 50 μg CPG2 i.p. in incomplete Freund's adjuvant followed by two injections of CPG2 in complete Freund's adjuvant (50 μg CPG2 each, i.p.) at monthly intervals and with two daily injections (50 μg and 100 μg in PBS, i.v.) 2 days before fusion. Immune spleen cells were fused with non-immunoglobulin secreting SP2/0 myeloma cells according to the hybridoma procedures of Köhler and Milstein (1975) *Nature* 256, 495.

The presence of anti-CPG2 antibodies was detected by a solid-phase indirect radioimmunoassay. A 1 μg ml$^{-1}$ solution of CPG2 in 0.05 M phosphate buffer was placed in polyvinyl microtitre plates (100 ng per well), allowed to dry, fixed with methanol and washed with PBS buffer containing a 0.05% Tween and 0.1% bovine serum albumin. Supernatant or purified antibody samples were diluted in PBS and incubated in the CPG2 coated microtitre plates (100 μl per well) at 37° C. for 4 h and then for 1 h with $^{125}$I-labelled rabbit anti-mouse IgG. The wells were washed three times with PBS-Tween buffer between each stage and after final washing individual wells were cut and counted in a gamma counter.

EXAMPLE 9
Bispecific Antibody Reactive Against CPG2 and CEA

The hybridoma producing $A_5B_7$, a monoclonal antibody reactive against CEA has been disclosed by Harwood et al (1986) *Brit. J. Cancer* 54, 75–82, and a method of generating a hybridoma producing SB43, a monoclonal antibody reactive against CPG2 is disclosed in the Examples.

The fusion protocol allows any two antibody-producing hybridomas to be fused and has been diclosed prevously (Clark & Waldmann (1987) *J. Natl. Cancer Inst.* 79, 1393–1401). Briefly, $5 \times 10^6$ to $3.5 \times 10^7$ cells of one parental hybridoma that have been previously rendered hypoxanthine/aminopterin/thymidine (HAT) sensitive by selection for a hypoxanthine phosphoribosyltransferase-negative variant were fused at 11:1 or 10:1 ratio, using 1 ml of a 50% (wt/vol) solution of polyethylene glycol, with the second parental hybridoma cells that had been pretreated with a lethal dose of 10 mM iodoacetamide. Excess polyethylene glycol was washed out and the cells were plated at concentrations from $8 \times 10^5$ per ml to $2 \times 10^5$ per ml into 24-well plates in bicarbonate-buffered Iscove's modified Dulbecco's medium (IMDM) supplemented with 5% (vol/vol) fetal calf serum. After 24 hr in culture, hybrid hybridomas were selected for in medium containing HAT.

EXAMPLE 10
Reduction of Residual Enzyme Activity at Non-Tumour Sites

It is desirable to inactivate the enzymatic portion of the enzyme-antibody conjugate at non-tumour sites, but not at the tumour. One method of achieving this effect is to administer to the patient being treated using the compounds of the invention antibodies raised against the enzyme portion which have been conjugated with galactose residues.

A monoclonal antibody (SB43) directed at CPG2 inactivates the enzyme. To prevent the antibody inactivating the enzymes at tumour sites additional galactose residues are conjugated to it so that it can still inactivate enzyme in plasma when it is given by intravenous route but the inactivating antibody is rapidly removed from the plasma and galactose receptors on hepatocytes.

The galactosylated SB43 is given to eliminate enzymic activity in plasma and then to give an amount of the non-galactosylated SB43 to inactivate residual enzyme activity in other non-tissues.

The monoclonal antibody SB43 is galactosylated using the following protocol: A stock solution of the activated derivative was made up as follows: Cyanomethyl 2,3,4,6-tetra-O-acetyl-1-thio-β-D-galactopyranoside (Sigma C-4141) [400 mg] in anhydrous methanol (10 ml) was treated with 5.4 mg of sodium methoxide in 1 ml of anhydrous methanol at room temperature for 48 hours. The mixture was kept in a 25 ml Quickfit (Trademark) conical flask fitted with a slightly greased stopper.

A stock solution of SB43 (1.3 mg/ml) was prepared in 0.25 M sodium borate buffer, pH 8.5. Aliquots of the required amount of activated galactosyl derivative (80, 40, 20, 10 μl) were dispensed into 3 ml glass ampoules and evaporated to a glassy residue in a stream of nitrogen. A solution of the antibody (200 μg) was added mixed until the residue was dissolved. After 2 hours at room temperature, the solution was dialvsed against three changes of PBS.

The preparations were scaled up by taking multiples of the volumes mentioned above.

I claim:

1. A therapeutic system comprising a compound comprising a target cell-specific portion and an inactivating-portion capable of converting a substance which, in its native state, is able to inhibit the effect of a cyotoxic agent into a substance which has less effect against said cytotoxic agent, a cytotoxic agent and a substance which in its native state is capable of inhibiting the effect of said cytotoxic agent and which can be converted by said inactivating portion into a substance which has less effect on the cytotoxic agent.

2. A therapeutic system according to claim 1 wherein the cytotoxic agent is either a folic acid antagonist and the substance capable of inhibiting the effect of said agent is folinic acid or an analogue thereof or the cytotoxic agent is a thymidine antagonist and the substance capable of inhibiting the effect of said agent is thymidine or an analogue thereof or it is a combination of both said antagonists.

* * * * *